(12) United States Patent
Conrad et al.

(10) Patent No.: US 8,182,475 B2
(45) Date of Patent: *May 22, 2012

(54) METHODS AND DEVICES FOR THE TREATMENT OF SKIN LESIONS

(75) Inventors: Robert Conrad, Houston, TX (US); Charles Conrad, Houston, TX (US)

(73) Assignee: LumaTherm, Inc., Austin, TX (US)

( * ) Notice: Subject to any disclaimer, the term of this patent is extended or adjusted under 35 U.S.C. 154(b) by 1619 days.

This patent is subject to a terminal disclaimer.

(21) Appl. No.: 11/541,805

(22) Filed: Oct. 2, 2006

(65) Prior Publication Data

US 2007/0088411 A1    Apr. 19, 2007

Related U.S. Application Data

(63) Continuation of application No. 10/677,737, filed on Oct. 2, 2003, now Pat. No. 7,137,979.

(60) Provisional application No. 60/474,821, filed on May 31, 2003.

(51) Int. Cl.
*A61B 18/04*    (2006.01)

(52) U.S. Cl. .................. 606/31; 606/29; 607/98

(58) Field of Classification Search ............ 606/27–31; 607/96, 98–102, 108–112
See application file for complete search history.

(56) References Cited

U.S. PATENT DOCUMENTS

| | | |
|---|---|---|
| 1,771,076 A | 7/1930 | Jacques |
| 1,817,823 A | 8/1931 | Ito |
| 2,533,955 A | 12/1950 | Pitts |
| 3,938,526 A | 2/1976 | Anderson et al. |
| 3,978,312 A | 8/1976 | Barton et al. |
| 4,074,110 A | 2/1978 | Slaughter |
| 4,090,517 A | 5/1978 | Takenaka |
| 4,106,478 A | 8/1978 | Higashijima et al. |
| 4,381,009 A | 4/1983 | Del Bon |
| 4,449,528 A | 5/1984 | Auth et al. |
| 4,582,057 A | 4/1986 | Auth et al. |
| 4,657,531 A | 4/1987 | Choi |
| 4,658,823 A | 4/1987 | Beddoe et al. |
| 4,691,703 A | 9/1987 | Auth et al. |
| 4,744,359 A | 5/1988 | Hatta et al. |
| 4,763,657 A | 8/1988 | Chen |
| 4,873,609 A | 10/1989 | Mackey |
| 4,878,493 A | 11/1989 | Pasternak et al. |

(Continued)

FOREIGN PATENT DOCUMENTS

CN    90225220.8    7/1991

(Continued)

OTHER PUBLICATIONS

Examination Report issued for Chinese Patent Application No. 200480018574.6; dated Nov. 16, 2007; 6 pages. (English Language translation).

(Continued)

*Primary Examiner* — Roy Gibson
(74) *Attorney, Agent, or Firm* — Dinsmore & Shohl LLP

(57) ABSTRACT

Methods and devices for the treatment of skin lesions resulting from bacterial, fungal or viral infections or from exposure to irritants are disclosed. The invention relates methods and devices for delivering a controlled dose of thermal energy to the infected or irritated tissue and thereby speed the recovery process.

16 Claims, 2 Drawing Sheets

U.S. PATENT DOCUMENTS

| | | |
|---|---|---|
| 4,944,297 A | 7/1990 | Ratkoff |
| 4,961,422 A | 10/1990 | Marchosky et al. |
| 5,038,769 A | 8/1991 | Krauser |
| 5,074,305 A | 12/1991 | Guderian |
| 5,097,828 A | 3/1992 | Deutsch |
| 5,169,384 A | 12/1992 | Bosniak et al. |
| 5,197,466 A | 3/1993 | Marchosky et al. |
| 5,235,990 A | 8/1993 | Dempsey |
| 5,327,886 A | 7/1994 | Chiu |
| 5,350,416 A | 9/1994 | Guderian |
| 5,421,816 A | 6/1995 | Lipkovker |
| 5,445,146 A | 8/1995 | Bellinger |
| 5,445,608 A | 8/1995 | Chen et al. |
| 5,459,298 A | 10/1995 | Tschakaloff |
| 5,496,356 A | 3/1996 | Hudz |
| 5,524,809 A | 6/1996 | Kosslow |
| 5,531,775 A | 7/1996 | Sasaki et al. |
| 5,662,624 A | 9/1997 | Sundstrom et al. |
| 5,688,266 A | 11/1997 | Edwards et al. |
| 5,755,757 A | 5/1998 | Teague |
| 5,792,211 A | 8/1998 | Teague |
| 5,800,504 A | 9/1998 | Bellifemine et al. |
| 5,817,139 A | 10/1998 | Kasano et al. |
| 5,830,211 A | 11/1998 | Santanna et al. |
| 5,849,029 A | 12/1998 | Eckhouse et al. |
| 6,022,346 A * | 2/2000 | Panescu et al. ............... 606/27 |
| 6,050,990 A * | 4/2000 | Tankovich et al. ............ 606/9 |
| 6,066,164 A | 5/2000 | Macher et al. |
| 6,090,788 A | 7/2000 | Lurie |
| 6,091,995 A | 7/2000 | Ingle et al. |
| 6,134,475 A | 10/2000 | Will |
| 6,162,217 A | 12/2000 | Kannenberg et al. |
| 6,187,263 B1 | 2/2001 | Nielsen |
| 6,235,027 B1 | 5/2001 | Herzon |
| 6,245,093 B1 | 6/2001 | Li |
| 6,253,104 B1 | 6/2001 | Jo |
| 6,283,931 B1 | 9/2001 | Augustine |
| 6,293,917 B1 | 9/2001 | Augustine et al. |
| 6,303,142 B1 | 10/2001 | Zhang et al. |
| 6,306,431 B1 | 10/2001 | Zhang et al. |
| 6,340,472 B1 | 1/2002 | Zhang et al. |
| 6,350,262 B1 | 2/2002 | Ashley |
| 6,465,006 B1 | 10/2002 | Zhang et al. |
| 6,465,709 B1 | 10/2002 | Sun et al. |
| 6,471,716 B1 | 10/2002 | Pecukonis |
| 6,485,506 B2 | 11/2002 | Augustine |
| 6,533,778 B2 | 3/2003 | Herzon |
| 6,587,731 B1 | 7/2003 | Ingle et al. |
| 6,589,270 B2 | 7/2003 | Augustine |
| 6,613,350 B1 | 9/2003 | Zhang et al. |
| 6,626,901 B1 | 9/2003 | Treat et al. |
| 6,629,974 B2 | 10/2003 | Penny et al. |
| 6,635,075 B2 | 10/2003 | Li |
| 6,708,060 B1 | 3/2004 | Avrahami et al. |
| 6,726,673 B1 | 4/2004 | Zhang et al. |
| 6,772,013 B1 | 8/2004 | Ingle et al. |
| 6,780,426 B2 | 8/2004 | Zhang et al. |
| 6,840,955 B2 | 1/2005 | Ein |
| 6,860,880 B2 | 3/2005 | Treat et al. |
| 6,908,463 B2 | 6/2005 | Treat et al. |
| 6,960,201 B2 * | 11/2005 | Cumbie ............................ 606/9 |
| 7,083,613 B2 | 8/2006 | Treat |
| 7,108,694 B2 | 9/2006 | Miura et al. |
| 7,177,695 B2 * | 2/2007 | Moran ........................... 607/50 |
| 2001/0008974 A1 | 7/2001 | Li et al. |
| 2001/0038993 A1 | 11/2001 | Lindquist |
| 2001/0041886 A1 | 11/2001 | Durkin et al. |
| 2001/0046654 A1 | 11/2001 | Zavitsanos et al. |
| 2002/0165472 A1 | 11/2002 | Augustine et al. |
| 2002/0165529 A1 | 11/2002 | Danek |
| 2002/0169442 A1 | 11/2002 | Neev |
| 2003/0036749 A1 | 2/2003 | Durkin et al. |
| 2003/0055475 A1 * | 3/2003 | Rousmaniere ................ 607/114 |
| 2003/0088298 A1 | 5/2003 | Li et al. |
| 2003/0097163 A1 | 5/2003 | Kane et al. |
| 2003/0125735 A1 | 7/2003 | Herzon |
| 2004/0127962 A1 | 7/2004 | Li et al. |
| 2004/0167498 A1 | 8/2004 | Azar |
| 2005/0048434 A1 | 3/2005 | Cipolla et al. |
| 2005/0203596 A1 | 9/2005 | Li et al. |
| 2005/0288748 A1 | 12/2005 | Li et al. |

FOREIGN PATENT DOCUMENTS

| | | |
|---|---|---|
| CN | 1113747 | 12/1995 |
| CN | 94116233.8 | 12/1995 |
| CN | 94221831.0 | 12/1995 |
| CN | 3050738 | 9/1996 |
| CN | 3067660 | 9/1997 |
| CN | 3072101 | 1/1998 |
| CN | 3108800 | 4/1999 |
| CN | 3150565 | 3/2000 |
| CN | 3165450 | 11/2000 |
| CN | 3168935 | 11/2000 |
| CN | 3210616 | 11/2001 |
| CN | 3231655 | 4/2002 |
| CN | 3355816 | 3/2004 |
| CN | 3360848 | 3/2004 |
| CN | 3388084 | 8/2004 |
| CN | 3503117 | 2/2006 |
| CN | 3506998 | 2/2006 |
| CN | 3517329 | 4/2006 |
| CN | 3134720 | 1/2007 |
| DE | 3880779 | 12/1993 |
| DE | 4331945 | 3/1995 |
| DE | 19808851 | 11/1998 |
| DE | 19752282 | 6/1999 |
| EP | 0 243 171 | 10/1987 |
| EP | 1231875 | 8/2002 |
| FR | 2689002 | 10/1993 |
| FR | 2720271 | 12/1995 |
| FR | 2746296 | 9/1997 |
| JP | 60005146 | 1/1985 |
| JP | 1288257 | 11/1989 |
| JP | 2104351 | 4/1990 |
| JP | 5248681 | 9/1993 |
| JP | 9187473 | 7/1997 |
| JP | 10229995 | 9/1998 |
| JP | 2001/120572 | 5/2001 |
| JP | 2001/276236 | 10/2001 |
| WO | WO-00/53113 | 9/2000 |
| WO | WO-01/34074 | 5/2001 |
| WO | WO-03/061497 | 7/2003 |
| WO | WO/2005/011777 | 2/2005 |

OTHER PUBLICATIONS

Russian Office Action issued for 2005141509, dated Apr. 2, 2008; 10 pages (with English Language translation).

Lowitt, Mark et al., "Pruritus", Seminars in Neurology—vol. 12, No. 4, Dec. 1992, 11 pgs.

Medical Letter on Drugs & Therapeutics, Consumers' Association, 1969 vol. 11 Pt 14, 2 pgs.

Medical Letter on Drugs & Therapeutics, Consumers' Association, 1966 vol. 8 Pt 13, 3 pgs.

Journal of Family Practice, 1987 vol. 25 Pt 5, 3 pgs.

Renee Glove et al., "Histamine release from rodent and human mast cells induced by protoporphyrin and ultravilet light: studies of the mechanism of mast-cell activation in erythropoietic protoporphyria", British Journal of Dermatology (1990) I22, 501-512, 13 pgs.

Bickford R.G., "Experiments Relating to the Itch Sensation, it's Peripheral Mechanism, and Central Pathways", Department of Clinical Research, University College Hospital Medical School, London, 1937, 13 pgs.

Field S.B. et al., "The Relationship Between Heating Time and Temerature: its Relevance to Clinical Hyperthermia", Radio Thereapy and Oncology, 1 (1983), 179-186, 8 pgs.

Ward, Louise et al., "A comparison of the effects of noxious and innocuous counterstimuli on experimentally induced itch and pain", Department of Physiology, St. Thomas' Hospital Medical Scholl (UMDS), London, 1996 Elsevier Science, 10 pgs.

Xu and Qian, "Analysis of Thermal Injury Process Based on Enzyme Deactivation Mechanisms," Journal of Biomechanical Engineering, Transactions of the ASME, vol. 117, pp. 462-465 (1995).

Home Health Products, http://www.safehomeproducts.com/SHP/HH/ItchZapper.asp., dated Aug. 13, 2003, 4 pgs.

Spectra Clear, Symedex Medical Spa Specialists, 2003, 2 pgs.

Convenience Translation with exhibit explanation: For Nullity Complaint against DE 59910543.7/EP 1231875 (covering exhibits NK1, NK2, NK3, NK4, NK5a, NK5b, NK6, NK7a, NK7b, NK7c and NK8), dated Mar. 28, 2008, 22 pgs.

Exhibit NK2, entitled "Feature Analysis of Claim 1", dated Mar. 28, 2008, (see convenience translation), 1 pg.

Exhibit NK3, Office Action dated Mar. 19, 2004, (see convenience translation), 18 pgs.

Exhibit NK4, Moritz et al, "Studies of Thermal Injury; The Relative Importance of Time and Surface Temperature in the Causation of Cutaneous Burns", (see convenience translation), vol. XXIII, Jul., Sep. and Nov. 1947, 27 pgs.

Exhibit NK7b, English translation for CN 1113747 (see convenience translation), 7 pgs.

Exhibit NK7c, printout showing CN 1113747 published on Dec. 27, 1995, (see convenience translation), 1 pg.

Translation of Objection from the Defendant Against the Nullity Action relating to the Patent EP 1231875/DE 59910543, dated May 23, 2008, 23 pps.

Exhibit NBK2, "Moxibustion—Methods of Therapy in Chinese Medicine", (see Translation of Objection from the Defendant Against the Nullity Action relating to the Patent EP 1231875/DE 59910543),dated May 23, 2008, 3 pgs.

Exhibit NBK1, "Analysis of Features of the disputed patent EP 2131875", (see Translation of Objection from the Defendant Against the Nullity Action relating to the Patent EP 1231875/DE 59910543), dated May 23, 2008, 1 pg.

Office Action issued for Russian Application No. 2005141509 dated Oct. 1, 2008, 7 pgs.

International Search Report and Written Opinion issued for PCT/US2008/073258; Dated: Nov. 24, 2008; 13 Pages.

Office Action issued for Singapore Application No. 200507726-8 dated Mar. 13, 2009, pp. 4.

Supplementary European Search Report issued for EP 04 75 3757, dated Jul. 28, 2009, 3 pages.

Levenberg, Alex et al., "Light and Heat Energy (LHE™) Technology—A Novel Approach to Nonablative Skin Rejuvenation", Radiancy © Apr. 2003, 4 pgs.

Elman, Monica et al., "Evaluating Pulsed Light and Heat Energy in Acne Clearance", Radiancy © Jun. 2002, 4 pgs.

\* cited by examiner

METHODS AND DEVICES FOR THE TREATMENT OF SKIN LESIONS

This application claims the benefit of U.S. Ser. No. 60/474,821, filed May 31, 2003, and is a continuation of application Ser. No. 10/677,737, now U.S. Pat. No. 7,137,979, filed Oct. 2, 2003.

BACKGROUND OF THE INVENTION

1. Field of the Invention

The invention relates to methods for the treatment of dermatological conditions in humans and animal via the controlled application of heat. In certain embodiments, the invention relates to methods of treating dermatological conditions caused or exacerbated by bacterial infection, and in particular, methods for the treatment of acne. The invention also relates to devices for the controlled application of heat for use in methods for treating dermatological conditions.

2. Description of Related Art

Skin infections and irritations pose significant health and cosmetic problems. Bacterial and fungal skin infections lead to common lesions such as acne, pimples and under-nail fungal infections. Other lesions are caused by irritants, which may be introduced as a result of bug bites or by exposure to other natural or man-made skin irritants. Still other skin lesions are caused by viral infection, a common example being the lesions known as "cold sores" or "fever blisters". These skin lesions are often unsightly and painful, and current methods of treatment are often inadequate.

Pustular eruptions, localized abscessed formation and local inflammatory conditions of the dermis and epidermis represent a particularly significant cosmetic and health problem. One of the most common afflictions of this type are lesion caused by the condition known as acne vulgaris. Acne vulgaris is associated with the Gram-positive anaerobic bacterium, *Propionibacterium acnes*. Acne afflicts 90% of all teenagers, and often continues to afflict men and women in the second, third and forth decade of life, sometimes persisting throughout adulthood. (Yonkosky, D. M. and P. E. Pochi, *Acne vulgaris in childhood. Pathogenesis and management.* Dermatol Clin, 1986. 4(1): p. 127-36.) Abscess formation from a number of primarily bacterial species (commonly *Staphylococcus* and *Streptococcus*) as well as fungal species, such as dermatophytes, are a less frequent medical and cosmetic problem but share similar challenges regarding effective treatment.

Setting the scene of acne and other skin infections, endogenous hormones (mainly androgens), which are present in unusually high concentrations in the blood during adolescence and puberty, give rise to an excessive production of sebum. This condition may worsen by a simultaneous increase in the rate of keratinization of the skin's horny layer (the stratum corneum). As the horny cells proliferate, they can form an occlusive plug or comedone which, coupled with the increased production of the sebum, represents an ideal medium for the proliferation of bacterial strains frequently resident on skin, such as *P. acnes*.

In acne vulgaris, plugged follicles eventually rupture, allowing discharge of their contents and causing local swelling and inflammation. The exposed follicles may darken from the deposition of pigment from damaged cells in the deeper layer of skin.

Acne vulgaris is therefore a chronic disorder of the pilosebaceous follicles characterized by comedones (blackheads), papules, pustules, cysts, nodules, and often results in the formation of permanent scars (Cunliffe, W. J., et al., *Comedogenesis: some aetiological, clinical and therapeutic strategies*. Dermatology, 2003. 206(1):11-6) that appear on the most visible areas of the skin particularly on the face, chest, back and occasionally neck, and upper arms. It is known that *P. acnes* also produces low-molecular-weight chemotactic factors which attract leukocytes, thereby causing or enhancing inflammation (Scholdgen, W., Hautarzt, 1965. 16(11): 518-20; Lever, L. and R. Marks, Drugs, 1990. 39(5):681-92). This increased inflammatory process, if left untreated, can produce significant immediate and long-term cosmetic problems including permanent scar formation.

Acne is a multistage condition. In its most severe form it leads to hospitalization of the patient, extensive discomfort and long term scaring of the skin.

Multiple treatment options have been available for acne and localized abscess formations (Scholdgen, W., Hautarzt, 1965. 16(11):518-20; Lever, L. and R. Marks, Drugs, 1990. 39(5):681-92) since the early 1960's, however no one drug appears effective against all distinctive types of acne or abscess formation and most preparations have significant side effects. (Russell, J. J., Am Fam Physician, 2000. 61(2):357-66.) Comedolytic agents, for example, promote comedonal drainage but also cause significant skin irritation. Topical antibiotics decrease the number of mild to moderate inflammatory lesions by inhibiting the growth of *P. acnes* and are also associated with skin irritation, dryness, and potential antibiotic resistance as well as potential overgrowth of fungal or yeast infections. (Gollnick, H. P. and A. Krautheim, Dermatology, 2003. 206(1):29-36.) Oral antibiotics are the standard for treating moderate to severe acne lesions, however, superinfection may occur with long-term exposure and may require routine laboratory monitoring. Antibiotic treatment against *P. acnes* has been the mainstay of treatment for more than 40 years. (Loveckova, Y. and I. Havlikova, Biomed Pap Med Fac Univ Palacky Olomouc Czech Repub, 2002. 146(2): 29-32.) Despite the widespread use of systemic antibiotics such as tetracyclines, erythromycins (Vermeulen, B., J. P. Remon, and H. Nelis, Int J Pharm, 1999. 178(1):13741) and clindamycins (Rizer, R. L., et al., *Clindamycin phosphate 1% gel in acne vulgaris*. Adv Ther, 2001. 18(6):244-52) as the most common, changes in the sensitivity of *P. acnes* to antibiotics has been seen for the last two decades. A number of mutations have been characterized which lead to increased resistance of *P. acnes* to both systemic and topical antibiotic treatments.

Another widespread treatment option for *P. acnes* has been the use of oral Vitamin A acid derivatives such as cis-Retinioc Acid (Accutane). However, the use of cis-Retinoic Acid has been reserved for severe cases of acne vulgaris since significant side effects can be seen with the use of cis-Retinioc acid. (Thorne, E. G., Br J Dermatol, 1992. 127 Suppl 41:31-6.) Some of these side effects include liver toxicity, severe skin drying, increase sensitivity to UV radiation, elevations in triglicyride and cholesterol levels, as well as mood changes including severe depression. Again, cis-Retinoic Acid has been reserved for severe or refractory cases of acne vulgaris.

In addition to prescription medications for the treatment of acne vulgaris, a number of over the counter topical preparations are widely used as well. (Scholdgen, W., Z Allgemeinmed, 1972. 48(17):833-5; Melski, J. W. and K. A. Arndt, Current concepts: topical therapy for acne. N Engl J Med, 1980. 302(9):5036; Lester, R. S., Topical formulary for the pediatrician. Pediatr Clin North Am, 1983. 30(4):749-65; Broniarczyk-Dyla, G. and C. Arkuszewska, Dermatol Monatsschr, 1989. 175(1):40-3; Zander, E. and S. Weisman, Treatment of acne vulgaris with salicylic acid pads. Clin Ther, 1992. 14(2):247-53; Kaye, E. T. and K. M. Kaye, Topical antibacterial agents. Infect Dis Clin North Am, 1995. 9(3): 547-59.)

These include, broadly, drying agents, oxidizing agents and astringents, also a wide variety of skin detergents and cleansers, as well as preparations, which attempt to form oxidizing agents which are reportedly toxic to *P. acnes*.

Other treatment methods that have been suggested include the methods disclosed in U.S. Pat. No. 6,183,500 involving the use of phototherapy in the treatment of acne vulgaris, whereby a concentrated light source is used as a treatment. Additionally, ultrasound devices to deliver energy in a localized fashion have also been described. (Ruiz-Esparza, J. and J. B. Gomez, Dermatol Surg, 2003. 29(4):333-9; discussion 339.) Even attempt of using cautery with local anesthesia has been described. (Pepall, L. M., M. P. Cosgrove, and W. J. Cunliffe, Br J Dermatol, 1991. 125(3):256-9.) Many of these devices require expensive and unwieldy equipment, and treatment by a physician.

Other types of bacterial skin lesions include bacterial folliculitis, (a localized infection of hair follicles) dermatitis, cellulitis, impetigo, ecthyma, furuncles and the like.

It has long been known that the application of heat to both pustular eruptions as well as localized abscesses can be an effective way to treat these conditions. The most common method employed uses hot compresses, which generally must be applied multiple times throughout the day to be even marginally effective. Often the use of hot compresses is recommended to alleviate discomfort by "popping," pimples and other pustular eruptions and allowing them to drain. Although it is well-known that the application of heat is toxic to multiple forms of bacteria, including *P. acnes* and *Staphylococcus* species, the use of hot compresses has shown limited utility in the treatment of skin lesions such as acne. In fact, many clinicians disfavor hot compresses because they are believed to aggravate acne. Furthermore, hot compresses are generally non-uniform in the amount of heat delivered. Over-heating of the compresses by the user may easily result in burns. Other disadvantages include the fact that hot compresses generally only maintain heat for a very limited period of time, and when moved about or reused may result in spread of infectious agents to healthy tissue.

A further type of skin lesion that has proved difficult to treat are viral skin lesions such as cold sores, also known as fever blisters. Cold sores are usually caused by strains of the Herpes Simplex virus and commonly result in lesions on and near the lips and inside the mouth of an infected individual. The sores are painful and unsightly, and like other facial lesions, frequently result in psychological stresses for the patients suffering from the condition. The eruption of the sores is often, but not always, preceded by a painful sensation that warns of an impending lesion.

Various ointments and skin treatments exist that may be used to reduce the painful symptoms of the sores and to decrease the time for the sores to heal. Certain anti-viral medications, such as Acyclovir and Famvir, may also be used to prevent outbreaks and reduce healing time. However these medications are generally expensive and only available with a prescription. Furthermore, they may result in adverse side effects such as renal toxicity and therefore physicians are sometimes reluctant to prescribe these medications for simple outbreak cases. Also, to effectively prevent a cold sore outbreak, the medications usually must be taken prophylactically or upon the first sign of an outbreak. Once the sore has erupted, the lesions generate infectious particles which may in turn infect other individuals. Alkali inhibition is commonly used for laboratory inhibition of Herpes viruses, but application of alkali is impractical in a clinical setting due to the harshness of the treatment to normal skin.

A further type of skin lesion are fungal infections, also known as fungal dermatitis, including conditions known medically as Tinea corporis, Tinea pedis, Tinea unguium, Tinea capitis, Tinea cruris, and Tinea barbae. Particularly troublesome is the condition known as *Tinea unguium* which is a fungal infection occurring under toenails or fingernails, a condition also referred to medically as onychomycosis or ringworm of the nails. Onychomycosis may be caused by several types of fungi, including *Trichophyton mentagrophytes, Candida albicans* or *Trichophyton rubrum*. Such infections are extremely difficult to treat effectively due to the difficulty in delivering effective amounts of antifungal medications to the area beneath the nail.

Onychomycosis can cause the nail to appear thickened and lusterless, and often causes nail discomfort. Also, the infected nail harbors a reservoir of pathogenic organisms which can spread to and re-infect other parts of the body, causing chronic diseases such as onychomycosis in other nails, athletes foot, foot dry skin and the like. Onychomycosis is prevalent throughout a large proportion of the population, with most of those afflicted from the ages of 40 years and older.

A human's nail has a nail plate, which is a hard outer surface of dead cells, and a nail bed below the nail plate. The nail plate is non-porous, whereas the nail bed is porous. There is soft flesh beneath the nail bed. The nail plate and the nail bed are relatively insensitive to pain. The underlying flesh is sensitive to pain. In onychomycosis, the nail plate, nail bed, and, in severe cases, the flesh below the nail bed can be infected.

Methods of treating onychomycosis include various methods of delivering medication to the nail bed, including various methods of introducing medication under or through the nail plate or of removing the nail plate partially or entirely to access the infected tissue. Other treatments include systemic anti-fungal medications. The difficulty with systemic medications is that they are not localized to the nail area and therefore it is difficult to achieve an effective dose without producing undesirable side effects in other parts of the body.

Tinea corporis, also known as tinea circinata or tinea glabrosa and referred to generally as ringworm of the body, is a fungal infection or dermatophytosis of the glabrous skin, i.e., areas of skin other than bearded area, scalp, groin, hands and feet, generally caused by fungal species such as those of *Microsporum* such as *Microsporum canis, Trichophyton* such as *Trichophyton rubrum, T. Mentagrophytes*, and *Epidermophyton*, particularly by the fungal species of *Trichophyton* and *Epidermophyton*. The condition generally includes the presence of one or more well-demarcated erythematous, scaly mascules with slightly raised borders and central healing, producing annular outlines. Various other types of lesions may also occur, such as those that are vesicular, eczematous, psoriasiform, verrucous, plaque-like, or deep.

Tinea cruris, also referred to generally as "jock itch" or ringworm of the groin, is a fungal infection or dermatophytosis of the groin, perineum and perineal regions, generally seen in males, and sometimes spreading to contiguous areas, generally caused by fungal species such as those of *Microsporum, Trichophyton*, and *Epidermophyton*, particularly by the fungal species of *Trichophyton* and *Epidermophyton*. The condition generally includes severely pruritic, sharply demarcated lesions with a raised erythematous margin and thin, dry scaling. Tinea cruris often accompanies tinea pedis (also known as "athlete's foot").

Tinea pedis results in interdigital lesions. Athlete's foot is an itching, malodorous, uncomfortable disorder resulting from large numbers of ordinary, nonvirulent bacteria proliferating in the fungus infected interspace.

Certain insect bites and contact with certain plants can expose skin to irritants that result in an itchy or painful immune response. The symptoms generally manifest soon after the introduction of the irritant, but can persist or sporadically reoccur for extended periods of time when the irritant is not effectively removed or inactivated by the immune response. Various treatments have been proposed for the treatment of the symptoms caused by these irritants. Typically the treatment involves that application of compounds that inhibit the immune response that generates the itching and inflammation usually associated with these conditions. These compounds tend to mask the symptoms of the insect bite without addressing the root cause of the irritation. They also tend to require repeated applications in order to obtain continuous symptom relief and frequently do not speed healing time in any appreciable manner.

For insect bites, a device has recently been marketed that is known as an "ItchZapper™". This device allegedly treats insect bites by applying one or more bursts of heat to the area of the bite thereby breaking down the irritants introduced by the insect bite and stopping the release of histamine. The device represented as heating to a temperature of 122° F., and insect proteins are said to break down at 118° F. The present inventors have tested this device and found it to be deficient for the treatment of insect bites in several respects. The ItchZapper™ device examined by the inventors rapidly heated to a peak temperature over a period of 2 to 4 seconds. The device cooled as residual heat bled off the device for a few seconds after the heating cycle was completed. The upward and downward ramping of the temperature was pronounced and the device was not capable of holding a sustained temperature for any appreciable period of time. The device never ramped to the same temperature twice, and when tested multiple times over relatively short period of time, the temperature often ramped beyond thermic damage for human skin (i.e. the device was capable of burning a subject). The total heating period for the device is well under 10 seconds. The extremely brief treatment period is unlikely to have any appreciable effect on insect bite symptoms without repeated treatments.

There is therefore a need for improved treatments for skin lesions caused by bacterial, viral and fungal infections and by exposure to irritants such as those introduced by insect bites and poisonous plants, particularly treatments that will effectively ameliorate the symptoms of the lesions and promote healing without causing adverse effects in the majority of patients.

BRIEF SUMMARY OF THE INVENTION

This invention relates to the use of a regulated heat source that can be applied to a skin lesion, such as pustular-form eruption or localized abscess, in order to accelerate the death of invading bacteria, fungi or viral particles, or to assist in the breakdown of a skin irritant and thereby speed the recovery process.

BRIEF DESCRIPTION OF THE SEVERAL VIEWS OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
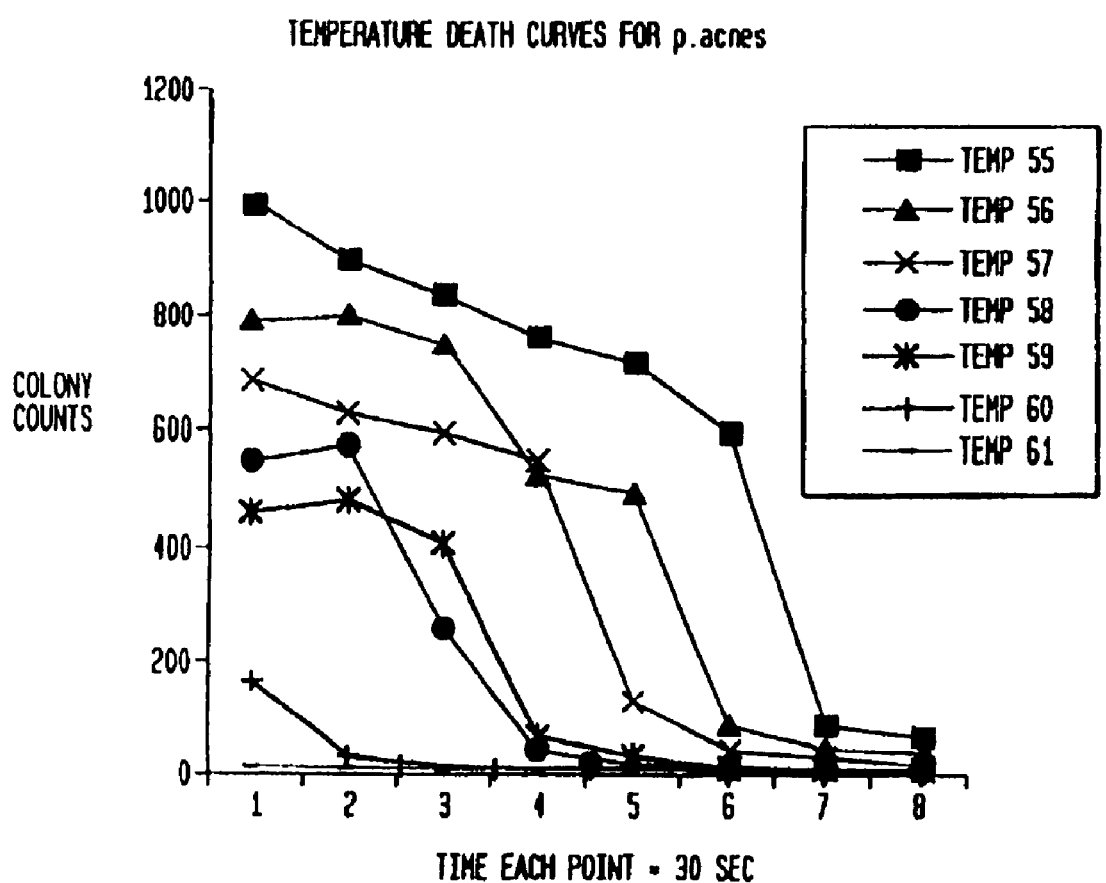
FIG. 1 shows temperature death curves for *P. acnes*.

The invention relates to methods and devices for the treatment of skin lesions involving the application of a controlled dose of thermal energy to the infected or irritated tissue and thereby speeding the recovery process. The invention can be used to treat skin lesions caused by bacterial, fungal or viral infections through the application of a regulated amount of heat. The invention can also be used to cause the thermal breakdown of certain skin irritants. For the purposes of the present invention "treating" a skin lesion means to slow, halt or even reverse the development of skin lesions and to reduce the lesion's healing time.

1. Lesions to Be Treated

A lesion according to the present invention is any infected or irritated tissue that can be effectively treated by the application of heat.

This invention provides methods and devices that are designed to deliver a regulated amount of thermal energy for a defined period of time. The controlled application of heat is optimized to hinder the progression of lesion formation, or to accelerate the healing of the lesion, or both, without causing thermal damage to the skin of the subject.

Skin lesions of the dermis, epidermis, follicle or other cutaneous structures can be treated by the methods and devices of the present invention, as well as skin lesions on mucosal surfaces such as the gums or other skin on the inside of the mouth. Additional skin structures in and around the finger or toe nails and cuticle are also potential sites prone to develop bacterial and fungal infections.

The lesions can be the result of infection by a bacterial strain including but not limited to strains such as *Propionibacterium acnes*, *Staphylococcus* species or *Streptococcus* species. In preferred embodiments, the present invention provides methods and devices for the treatment of skin lesions such as the kind commonly associated with acne vulgaris. These skin lesions include pustular eruptions and localized abscesses such as cysts, nodules, pustules, papules, comedones (blackheads) and the like. These lesions include those that are commonly referred to as pimples, whiteheads, zits, acne and the like.

Alternatively or additionally, the lesions can further be result of infection by fungal species, including but not limited to fungal species capable of producing conditions such as toenail or fingernail infections, ringworm and the like. These fungal species include *Microsporum* species such as *Microsporum canis*, *Trichophyton* species such as *Trichophyton rubrum*, *Trichophyton*. *Mentagrophytes*, *Epidermophyton* species, *Candida albicans*, and the like. Such fungal species are sometimes referred to broadly as "dermatophytes".

Alternatively or additionally, in other embodiments, the skin lesions can be the result of viral infections, including infections caused by Herpes viruses such as *Herpes simplex* types I and II (cold sores and genital herpes), *Varicella zoster* (chicken pox) and the like.

While not bound by theory, it is believed that treatment of skin lesions caused by bacterial, fungal and viral infections can be effectively treated by the application of controlled quantities of heat either by the stimulation of a "heat-shock"

response in the microorganism resulting in its death, impairment, dormancy or other loss of viability of the infectious agent.

Alternatively or additionally, embodiments of the present invention provide methods and devices for the controlled application of heat for the treatment of skin lesions caused by an irritant. Common skin irritants that can be treated by the present invention include those introduced by bug bites, such as mosquito, chigger, ant, spider bites, scabies and the like. Other skin irritants introduced by other animal species, such as jellyfish, snakes and the like, or by plants such as poison ivy, poison oak, poison sumac and the like, can also be treated using the methods and devices of the present invention. Not be limited by theory, the application of regulated quantities of heat can result in the biochemical denaturation of the foreign irritant proteins, or can disrupt the host reaction to the particular irritant, or both. The disruption of the host reaction can occur by the heat producing an affect on the cellular response to the foreign material.

The methods and devices of the present invention provide the application to a lesion of an amount of heat (thermal energy) wherein the heat is applied over one or more treatment periods in an amount sufficient to result in improved recovery times for the treated lesion. An effective therapeutic amount is therefore any application or applications of heat that are capable of measurably decreasing average recovery times for a given type of skin lesion, preferably by improving the average recovery time by 1, 2, 3, 4, 5 or more days, preventing nascent outbreaks of new lesions, and additionally or alternatively, appreciably or substantially reducing the discomfort associated with the lesion, such as itching or sensations of pain, pressure, heat and the like.

2. Methods of Treating Skin Lesions

In certain embodiments, the present invention provides a method of treating skin lesions resulting from fungal or bacterial infection or from exposure to skin irritants by applying an amount of heat effective to raise the temperature of the lesion or tissue to be treated to a therapeutically effective temperature range between 38° C. to 67° C., with a more preferable range of between about 43° C. to 67° C. Other preferable ranges of therapeutically effective temperatures are ranges having a lower bound of about 38, 39, 40, 41, 42, 43, 44, 45, 46, 47, 48, 49, 50, 51, 52, 53, 54, 55, 56, 57 or 58° C. and an upper bound of about 50, 51, 52, 53, 54, 55, 56, 57, 58, 59, 60, 61, 62, 63, 64, 65, 66 or 67° C. The optimal temperature range for the treatment of a specific lesion can readily be determined by those of skill in the art through routine methods such as testing appropriate infectious organism in culture, testing of the thermal lability of an irritant or by the testing of live subjects experiencing skin lesions of a specific type.

For the treatment of viral skin infections such as cold sores, the regulated amount of heat to be applied can be sufficient to heat the infected tissue to a therapeutically effective temperature range between 38° C. and 67° C. Other preferable ranges of therapeutically effective temperatures are those having a lower bound of about 38, 39, 40, 41, 42, 43, 44, 45, 46, 47, 48, 49, 50, 51, 52, 53, 54, 55, 56, 57 or 58° C. and an upper bound of about 42, 43, 44, 45, 46, 47, 48, 49, 50, 51, 52, 53, 54, 55, 56, 57, 58, 59, 60, 61, 62, 63, 64, 65, 66 or 67° C. The optimal temperature range for the treatment of a specific lesion can readily be determined by those of skill in the art through the routine testing of the appropriate viral cultures or by the testing of live subjects experiencing skin lesions of a specific type.

The infected tissue is heated to the appropriate temperature range for a period of at least 5 seconds, preferably at least 10 seconds, at least 15 seconds, at least 20 seconds, at least 25 seconds, at least 30 seconds, at least 40 seconds, at least 50 seconds, at least 60 seconds, at least 90 seconds, at least 2 minutes, at least 2 and ½ minutes, at least 3 minutes, at least 3 and ½ minutes, at least 4 minutes, at least 5 minutes, at least 6 minutes, at least 7 minutes, at least 10 minutes, at least 15 minutes or at least 20 minutes. In preferred embodiments, the infected tissue must continuously remain heated to one or more temperatures within the appropriate treatment range for the duration of the treatment period. The optimal period of time during which a specific type of lesion should be heated to a temperature within the appropriate temperature range can readily be determined by those of skill in the art through routine methods such as testing responses of the appropriate infectious organism in culture, testing of the thermal lability of an irritant or by the testing of live subjects experiencing skin lesions of a specific type.

In alternate embodiments, the effective therapeutic amount of heat to be applied to an infected tissue can be determined by empirical testing. Any effective method known to those of skill in the art can be used to deliver heat to the infected tissue, so long as the amount of heat delivered is low enough to avoid inflicting unacceptable levels of thermal damage (burns) and high enough to aid in the prevention or recovery process. In general, the application of greater amounts of heat will require shorter application periods to be effective, while the application of lower amounts of heat will require longer application periods. In any case, however, the amount of heat will have to meet the critical threshold of being an amount sufficient to appreciably or substantially alter healing times, most preferably by improving the average recovery time by at least 1, 2, 3, 4, 5 or more days, or by preventing nascent outbreaks before they result in pustular eruptions, sores or other types of skin lesions.

3. Devices for the Treatment of Skin Lesions

The devices provided by the present invention are heating devices, preferably, electrical heating devices, that are capable of delivering a regulated supply of thermal energy to a lesion for a period of time sufficient to deliver an effective therapeutic amount of heat.

The devices of the present invention comprise an interface for contacting the skin of a subject and a heater capable of heating the interface to a temperature between 38° C. and 67° C. and sustaining one or more temperatures within that range for at least 5 seconds.

A "subject" for the purposes of the present invention is a human or animal having a lesion that can be effectively treated by the application of heat. A "user" is a person who uses a device of the present invention to apply an effective therapeutic amount of heat to a lesion. In certain embodiments, the user can be the subject, such as where the user is applying the device to a lesion on the user's own body. Alternatively the user can be an individual other than the subject, who applies the device to a lesion found on another, for example, a child or patient.

In certain embodiments, the device is capable of heating the interface to a regulated temperature between 38° C. and 67° C. According to the present invention, a regulated temperature is one that does not significantly depart from the desired treatment range during the time period required for treatment of the lesion. Preferably the interface can be heated to a desired temperature range having a lower bound of about 38, 39, 40, 41, 42, 43, 44, 45, 46, 47, 48, 49, 50, 51, 52, 53, 54, 55, 56, 57, 58, 59, 60, 61, 62, 63, 64, 65 or 66° C. Further, the interface is preferably heated to a desired temperature range having an upper bound of about 39, 40, 41, 42, 43, 44, 45, 46, 47, 48, 49, 50, 51, 52, 53, 54, 55, 56, 57, 58, 59, 60, 61, 62, 63, 64, 65, 66 or 67° C. The optimal temperature range for a particular treatment device can readily be determined by those of skill in the art through routine methods such as the testing of the treatment device on live subjects having lesions of the type intended to be treated by the device.

Although thermal damage generally occurs when human skin is heated to a temperature of approximately 66° C. (150° F.) or greater, an interface heated to this temperature or a higher temperature can nevertheless deliver an effective therapeutic amount of heat to a lesion without resulting in thermal damage, depending on the amount of thermal energy delivered over a particular surface area and how readily the thermal energy is dissipated by the heated tissue.

(a) The Interface

The devices of the present invention comprise an interface which act as a conduit through which heat generated by a heater is delivered to the lesion or skin tissue being treated.

While the interface of the present invention can be applied directly to the skin of a subject, in certain embodiments there can be one or more intervening layers between the skin of the subject and the interface. The intervening layer or layers can be any desired substance capable of allowing transmission of thermal energy. In particular, an intervening layer can be composed of a solid, semi-solid or liquid layer. In certain preferred embodiments, such an intervening layer can comprise a sterilizable or disposable covering for the interface which is intended to prevent the transmission of infectious agent from one use to the next. In other embodiments, the intervening layer can be a bandage or other dressing on the lesion. In still further embodiments, the intervening layer can be biological material such as a fingernail or toenail, for example, when using the device for the treatment of a fungal infection present under the nail.

In alternate embodiments, the device of the present invention can be sterilized by heating the device to a high enough temperature and for a sufficient period of time to result in loss of viability of any microorganisms that are present on the surface of the interface. In other embodiments, the sterility of the interface can be enhanced by using an interface composed of metal or other materials that are inhospitable to the survival of microorganisms such as bacteria. In still further embodiments, the interface itself can be interchangeable, disposable, or otherwise capable of being sterilized e.g. by conventional methods of sterilization such as application of an antiseptic to the surface to be sterilized.

The interface of the present invention is the portion of the device intended to come in direct or indirect contact with the skin or tissue of the subject. The interface can be any of any configuration that will allow effective transmission of heat to the area to be treated. The interface can have a surface area of greater than 100 cm$^2$, 50 cm$^2$, 20 cm$^2$, 10 cm$^2$, 5 cm$^2$, 2 cm$^2$, 1 cm$^2$, 0.5 cm$^2$, 0.3 cm$^2$, 0.2 cm$^2$ or 0.1 cm$^2$ surface area, or the interface can be smaller than 0.1 cm$^2$. The interface can have a surface area less than 500 cm$^2$, 200 cm$^2$, 100 cm$^2$, 50 cm$^2$, 20 cm$^2$, 10 cm$^2$, 5 cm$^2$, 2 cm$^2$, cm$^2$, 0.5 cm$^2$, 0.3 cm$^2$, 0.2 cm$^2$ or 0.1 cm$^2$ or the surface area can be larger than 500 cm$^2$. In general, devices having larger interfaces will be desirable for the treatment of multiple lesions on a single subject, while devices having interfaces with smaller interfaces will be desirable for the treatment of a few or a single lesion. The use of smaller interfaces will in certain circumstances be desirable as a means to reduce any discomfort that may be experienced by the subject during treatment, particularly when treatments at higher temperatures or for longer time periods are desirable for the treatment of a particular type of lesion.

The shape of the interface can be any shape and composed of any material that is appropriate for the treatment of a particular type of lesion. In particular, where the interface is composed of a inflexible or substantially inflexible material, the interface can be substantially planar, convex or concave. For example, the interface of a device intended for the treatment of pustular eruptions or localized abscesses on the face might preferably be substantially planar or convex so as to come in contact with one or more lesions and possibly their immediate surroundings. A device for the treatment of fungal infections of the toenail might preferably be shaped as a ring, arc, cap, or other appropriate shape so as to be placed in close proximity to the infected tissue. Other shapes for the interface will be readily apparent to those of skill of the art depending on the types of lesions intended to be treated with the devices of the present invention.

(b) Heat Source

The present invention provides devices having one or more heaters intended to provide therapeutic heat according to the methods disclosed herein.

In preferred embodiments, the heater includes a semiconductor device, such as a transistor running in it's linear range. In certain arrangements of the present device, the semiconductor device can dissipate power as heat and transfer the heat directly or indirectly to one or more heat sinks. The heat sink or sinks, in turn, can serve to transmit the heat to the lesion.

In other embodiments, the heater can include a cartridge heater, a lamp or light bulb, a foil-type heater attached to a thermal mass, or any other type of heat source capable of operating in the desired voltage or temperature range. Such heat sources can be used to apply heat directly to the lesion or can be connected to one or more heat sinks capable of transmitting heat to a lesion.

Numerous types of heaters that can be used in the present invention will be apparent to those of skill in the art. Any heating system capable of generating amounts of heat appropriate for the methods of the present invention can be used as a heat source for the treatment of skin lesions.

Preferred devices of the present invention include devices having a heater capable of heating the interface to a sustained and constant temperature, devices capable of ramping temperature up during the treatment period, devices capable of ramping temperature down during the treatment period, and devices capable of varying the temperature in a regulated manner, all in such a manner that the temperature of the interface never departs from the desired temperature range during one or more treatment periods. In certain embodiments, devices capable of ramping the temperature up in a regulated manner are particularly desirable. Some subjects experience minor discomfort from the application of certain therapeutic amounts of heat. This discomfort can often be alleviated or eliminated entirely by devices that gradually ramp up to the desired treatment temperature range. The interface of the device, in certain embodiments, can be gradually heated to the desired treatment temperature or temperatures while in contact with the subject's skin. In alternate embodiments, the interface is heated to the desired temperature range and is then applied to the lesion.

(c) Power Source

The heater used in the devices of the present invention generate heat through the use of some type of power source. In preferred embodiments, the power source for the heater is electrical in nature. Such electrical devices can be powered by alternating current or by direct current. In certain embodiments, portable power sources can be used, such as batteries. In other embodiments the device can be powered by means of connection to a conventional alternating current outlet.

Electrical devices of the present invention can include an integrated circuit capable of regulating the transfer of heat to the interface in an accurate and sustained manner. In certain embodiments the device can further comprise a means of detecting the present temperature of the interface and regulating the amount of heat transferred to the interface based on the actual temperature of the interface and the temperature needed for a particular application.

The source of the electrical current for the electrical devices of the present invention can be either internal or external to the device, or a combination of the two. Internal power sources include rechargeable and non-rechargeable battery systems, and the like. External power sources can include either alternating current or direct current power sources.

In certain embodiments having an internal power source, the electrical device of the present invention is powered using batteries, preferably commercial disposable or rechargeable batteries, including conventional alkaline and lithium-type batteries and the like. In other embodiments, the internal power source is a rechargeable battery system that is not intended to be replaced by the consumer. Such embodiments could be sold in conjunction with one or more devices—for recharging the battery system. In preferred embodiments the battery system can be recharged by connecting the battery system to an alternating current power source via the battery recharging device.

In certain embodiments having an external power source, the electrical device can include a power cord and plug for attaching the system to an electrical current power source such as a conventional wall outlet.

The electrical power source of the electrical device of the present invention can be any power source that can be adapted by one of skill in the art to the present application. For example, in the case of embodiments making use of one or more batteries, the number of battery cells can be adjusted according to the power needs of the heating system of the device, or in order to optimize the intervals between required battery replacement or recharging. Methods of designing a device for use in conjunction with various electrical power sources will be readily apparent to one of skill in the art.

(d) Heater Control System

In certain embodiments, the electrical devices of the present invention can include a heater control system designed to monitor and, additionally or alternatively, to adjust the heater temperature to maintain the optimal temperature range of the heater and, additionally or alternatively, one or more heat sinks. The Heater Control Systems of the present invention include those that use feedback controls such as "on-off" control, proportional control, proportional-derivative (PD), proportional-integral-differential (PID) control and the like to establish, maintain or adjust the temperature of the interface during heating. In preferred embodiments, the heater control system uses PID algorithms to directly or indirectly control the temperature of the interface. Although PID control mechanisms are the preferred embodiment, other mechanisms for monitoring, adjusting or maintaining the temperature of the device at a desired temperature or within a desired range will be apparent to those of skill in the art.

The heater control system can therefore be any system capable of maintaining the temperature of the interface within a desired range or for preventing the interface from substantially exceeding a desired temperature. The heater control system can also be used to ramp the temperature of the device up or down in a controlled manner over a desired period of time. For example, the heater control system can be used to rapidly bring the interface to a desired temperature and to maintain that temperature for the desired treatment period. Alternatively, the heater control system can be used to heat the device in a gradual manner (particularly in embodiments of the present invention wherein the device is applied to the skin at a lower temperature and gradually ramped up to a desired therapeutic temperature in order to minimize the discomfort of the subject during treatment).

Devices containing heater control systems are particularly preferred embodiments of the present invention because they alleviate many of the safety concerns engendered by skin heating devices such as conventional hot compresses. Depending on their design, conventional heating devices may be easily overheated under normal or common operating conditions, resulting in potential harm or serious discomfort to the subject. Preferred heater control systems of the present invention are those capable of substantially maintaining the temperature of the interface within the desired therapeutic temperature range and, additionally or alternatively, those that contain control mechanisms that render the device incapable of heating the interface to a temperature dangerous or harmful to the subject.

In particular, it is most desirable that under normal or common operating conditions the heater control mechanism prevent the interface from substantially overshooting the desired high temperature for a particular type of treatment. It is especially preferred that the device be incapable of heating skin to a temperature greater than or equal to the temperature at which the skin becomes thermally damaged. Not to be bound by theory, it is believed that for most subjects that temperature is approximately 66° C. (150° F.).

It is also desirable that the heater control system be capable of regulating the temperature of the interface such that the interface remains in the desired temperature range for a period of at least 5 seconds, at least 10 seconds, at least 15 seconds, at least 20 seconds, at least 25 seconds, at least 30 seconds, at least 40 seconds, at least 50 seconds, at least 60 seconds, at least 90 seconds, at least 2 minutes, at least 2 and ½ minutes, at least 3 minutes, at least 3 and ½ minutes, at least 4 minutes, at least 5 minutes, at least 6 minutes, at least 7 minutes, at least 10 minutes, at least 15 minutes or at least 20 minutes.

(e) Input/Output System

Devices of the present invention can be programmable or adjustable. In certain embodiments, the present invention includes an input/output system. In preferred embodiments, the means of programming or adjusting the temperature of the device can be integrated circuitry and additionally or alternatively a thermostat control. However any means of allowing the user to controlling the function of the device known to those of skill in the art can be used in the present invention.

At its most rudimentary, the input/output system is merely a means of connecting the heater to the power source and thereby heating the interface. For example, the input/output system can comprise some sort of on/off switch accessible on the exterior of the device. More complex systems include those having push buttons, touch pads, dials, switches or other types of input mechanisms whereby a user can activate preprogrammed settings of the device and additionally or alternatively program or set the device to apply heat in a desired fashion. The input device therefore can allow the user to adjust the function of the device in a variety of ways: to limit the period of time for which the device is heated, adjust the temperature of the interface, or otherwise alter the manner in which the device delivers heat. For example, the input/output system can be designed to allow the user to direct the device to heat to a specified temperature, then ramp the temperature up at a certain rate and then hold the temperature of the interface constant when a desired final temperature is reached. In preferred embodiments, the input/output system can allow the user to adjust the temperature of the interface to any temperature within the safe operating range of the device. In other embodiments, the input/output system can be pre-programmed with a plurality of settings optimized by the manufacturer of the device for the treatment of particular types of lesion.

More sophisticated input/output systems can optionally include a timer. Said timer can be used for indicating to a user that a desired time period had elapsed, for regulating the heating of the device for a defined period of time, or for any other purpose that might be of assistance to the user. For example, the device could have a timer that indicates that the recommended or desired treatment period for a lesion had elapsed. Such a timer could be programmable by the user or could be accessed through pre-programmed settings. In alternate embodiments, the device can be programmed to have different settings that change the temperature range that the device is heated to, settings that maintain a constant temperature or vary the temperature in a desired manner, and additionally or alternatively, settings that provide programmable or pre-programmed application times.

Where it is desirable that the device be pre-heated to a certain temperature prior to application, the input/output system can have a means of informing the user that device is ready for use. For example, the input/output system can comprise a sensor for determining that the appropriate temperature has been reached and an indicator to inform the user that the device is ready for use.

Similarly, the device can also comprise a safety system for indicating to the user that the device has been heated beyond the desired temperature range and should not be used until the temperature has been reduced appropriately. The device can contain a further indicator for informing the user that a safe operating temperature has been reached, or alternatively, the warning indicator for the safety system can be deactivated when the device is no longer heated above the desired temperature.

Timers or other indicators of the present invention can be visual indicators such as lights, LEDs, LCD displays and the like, auditory indicators such as a bell, buzzer or the like, tactile indicators such as vibrators and the like, or any other type of indicator known to those of skill in the art.

As discussed previously, the devices of the present invention can be programmed or adjusted to maintain temperatures within an effective therapeutic range. The input/output system can provide a means of varying the amount of heat provided by the device according to the therapeutic needs of a particular lesions or individual. For example, the therapeutic range required for the treatment of certain bacterial infections might be higher than that required for the treatment of certain viral lesions. Similarly, the amount of time for which heat should be applied can also vary according to the type of lesion or individual. The input/output system can provided a means of controlling the application of heat in a manner determined to be optimal for a specific lesion, the age or skin sensitivity of the subject or for otherwise adjusting the device according to the needs or desires of a particular user.

If desired, the input/output system can be further programmed to have a sterilization setting. For example, such a setting might be used to heat the interface to a high enough temperature and for a sufficient period of time to ensure that no microorganisms residing on the surface of the interface are likely to have survived.

The input/output systems of the present invention can be effected through the use of microprocessors or other supporting electronics. Numerous structures and designs for input/output systems appropriate for use in the present invention will be readily apparent to those of skill in the art.

(f) Body

The body of the device can be a structure for providing a handle or other means of effectively handling the device. It can also serve to shield the heater, power source or other electrical components of the device from direct contact by the user during the operation of the device. In preferred embodiments, the design of the body of the device will allow a user to safely and effectively apply heat to a specific area to be treated. The body of the device can be any acceptable shape, as determined by the intended use of the device. In certain preferred embodiments, the body of the device is of a size and shape that fits comfortably in the hand of a user, for example, a substantially cylindrical shape having a handle at one end and the interface at the other. In other embodiments the device is shaped as a pad or panel that is applied to a surface area to be treated. Such a pad or panel could have one or more heated faces that acts as the interface of the device and one or more insulated or un-heated faces that act as a handle or contact point for controlling the application of the interface. In still further embodiments, the device can be designed to conform to a surface area to a particular surface area to treated, for example a curved or ring shaped structure meant to fit over a toenail or toe, or a fingernail or finger. For example, a device could be designed for treating an infected toe wherein the device comprised a cap having at least one inner face for delivering a therapeutic amount of heat to the affected area of the toe and an insulated or un-heated outer face that allows safe and effective handling of the device by the user. Other configurations will be readily apparent to those of skill in the art and any structural arrangement that allows the user to safely and effectively apply heat to a lesion to be treated are provided by the present invention.

An exemplary arrangement of the elements of the present invention would be an electrical device comprising a cylindrical body wherein an interface was disposed at one end of the body. The opposite end of the device forms a grip of handle for the user. Disposed along the sides or at the opposite end of the device there are optionally one or more input devices allowing the user to turn the device on and activate one or more pre-programmed treatment settings. One or more indicators inform the user when the device is ready to begin the treatment cycle and when the treatment cycle is complete. The exemplary device further comprises an electrical power source powered by a rechargeable battery. As can be readily perceived by those of skill in the art, this exemplary arrangement is but one of the possible combinations of the features described above. A multitude of arrangements will be readily apparent to those of skill in the art that will meet the objectives of the device of the present invention.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Temperature Dependent Death Curves for *P. acnes*.

Materials and Methods: The bacterial strain *P. acnes* was purchased from The American Type Culture Collection ATCC (No. 11827, Lot 419571, Manassas, Va.). The cultures were stored in KWIK-STIK lyophilized preparations. The lyophilized cells (*P. acnes*) were rehydrated according to the manufacturers recommendations and initially grown on a streak plate to isolate individual colonies under anaerobic conditions. These plates were then incubated overnight at 37° C. in an anaerobic chamber. Individual colonies were then isolated and inoculated into TSB-growth media with medium agitation overnight. From these aliquots of 0.1 ml of TSB broth culture was added to the 0.9 ml of PBS sterile buffer. This mixture was then transferred to thin-walled Eppendorf 1.5 ml tubes and placed in a heating block at various times and temperatures. The cultures after specific incubation times were removed and 0.1 ml of the material was plated onto TSA plates. This mixture was then spread with a sterile hockey-stick and then allowed to incubate at 37° for 5 days in anaerobic conditions. The plates were then removed and colonies were counted and recorded. The results are demonstrated in FIG. 1. FIG. 1 demonstrates the rapid decline of *P. acnes* in response to various temperatures and duration of treatment. The baseline *P. acnes* colony count that had not been exposed to the heat source was 1050.

Results: A general trend of reduction of required time to kill the bacterial strain is seen at higher temperature incubations. Also of note is the temporal thermal threshold where the number of colonies drops off in a very steep fashion. By using the curves generated by such experiments the optimal thermal output and the timing for each temperature can be extrapolated for a localized heating device. The in vitro data shown demonstrates significant sensitivity of *P. acnes* bacterial cells to the effects of sustained low-level heat. Temperatures of 55° C. result in the death of substantially all of the bacteria after 3½ minutes. Temperatures of 58 and 59° C. result in the death of substantially all of the bacteria after 2 minutes. These curves demonstrate that *P. acnes* can be rendered largely non-viable by treatment under the conditions shown by the death curves.

EXAMPLE 2

Treatment of acne lesions in human subjects. The inventors have performed preliminary studies on over 100 volunteers experiencing outbreaks of acne lesions. All subjects reported being satisfied with the results obtained. The results showed a clear response to treatment in approximately 90% of subjects treated. No subject reported any serious adverse effects due to treatment. Furthermore, we have discovered a treated lesion heals more than 80% faster than untreated lesions.

The electrical device used in the present study had an interface of approximately 0.4 $cm^2$. The interface of the device was heated to a constant temperature of approximately 48-50° C. prior to application of the device to the skin surface, and the temperature was maintained during the treatment period. Each of the subjects were given instructions on how to use the device and were monitored during the treatment. The treatment consisted of a 2½ minute application of the device to the lesion site. The study called for the application of two treatment cycles to each patient, with the second treatment cycle being administered 12 hours after the first. In practice, however, the treatments were frequently only conducted once on each subject because twelve hours after the first treatment many of the lesions had healed to an extent that they did not require any further treatment.

Figure 2:
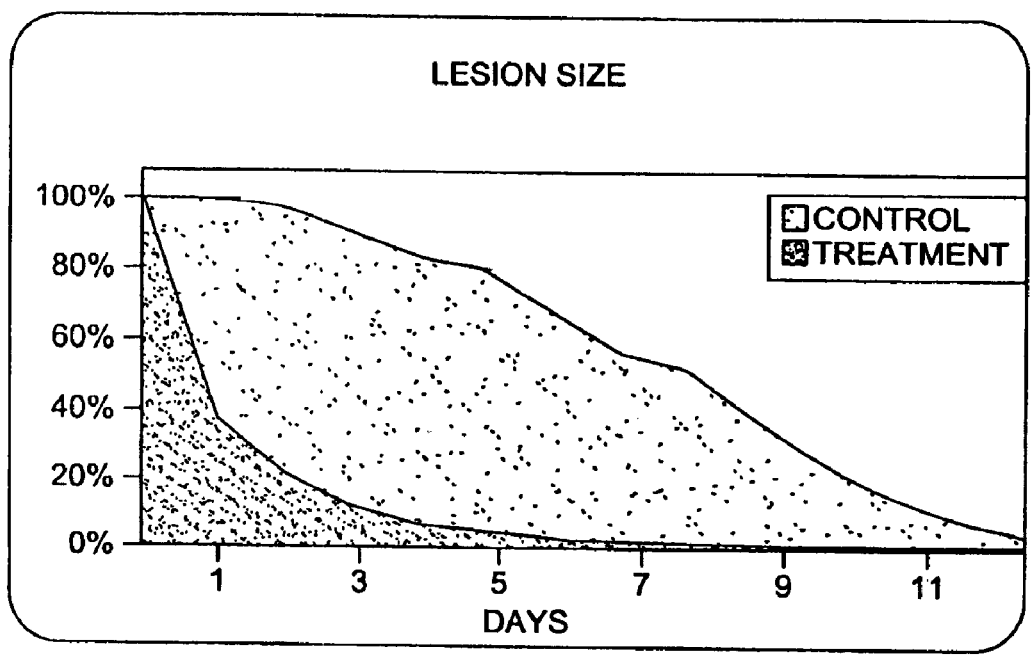
FIG. 2 shows a comparison of control and treatment response for human subjects suffering from acne lesions.

Results of experiments performed on volunteer subjects are listed in Table 1. Members of the control group were not treated. Members of the treatment group were treated as described above. Both groups either examined or self-reported the results of treatment over the following 14 days. Only results from study participants who reported data for 14 days was included in the table. The data is reported in terms of the size of the lesion prior to treatment. A lesion size of 100% indicates that the lesion size was unchanged. Lesion size was approximated in increments of 10%. A lesion size of 0% indicates that the lesion had fully healed. The averaged results for the control group and treatment group is graphed in FIG. 2. As shown by the figure, preliminary results indicate that the treatment resulted in a dramatic decrease both in lesion size and overall healing time.

TABLE I

| # | Name | Gender | Age | Day 1 | Day 2 | Day 3 | Day 4 | Day 5 | Day 6 | Day 7 | Day 8 | Day 9 | Day 10 | Day 11 | Day 12 | Day 13 | Day 14 |
|---|------|--------|-----|-------|-------|-------|-------|-------|-------|-------|-------|-------|--------|--------|--------|--------|--------|
| | | | | | | | Control Group | | | | | | | | | | |
| 1 | LEF | F | 27 | 100% | 100% | 100% | 100% | 90% | 90% | 80% | 80% | 50% | 20% | 10% | 0% | 0% | 0% |
| 2 | AMC | F | 22 | 100% | 100% | 100% | 90% | 90% | 80% | 80% | 60% | 40% | 40% | 20% | 20% | 20% | 10% |
| 3 | AWC | F | 16 | 100% | 100% | 100% | 100% | 100% | 100% | 100% | 80% | 80% | 60% | 40% | 10% | 10% | 10% |
| 4 | KAC | F | 13 | 100% | 100% | 100% | 80% | 80% | 70% | 40% | 40% | 40% | 40% | 20% | 10% | 0% | 0% |
| 5 | ECP | F | 35 | 100% | 100% | 100% | 100% | 80% | 80% | 80% | 20% | 20% | 20% | 20% | 10% | 0% | 0% |
| 6 | KSL | F | 21 | 100% | 100% | 90% | 90% | 80% | 80% | 60% | 60% | 60% | 30% | 30% | 10% | 10% | 0% |
| 7 | NET | F | 18 | 100% | 100% | 100% | 80% | 80% | 80% | 60% | 60% | 60% | 30% | 30% | 30% | 10% | 10% |
| 8 | LHJ | F | 27 | 100% | 100% | 100% | 80% | 80% | 80% | 50% | 50% | 50% | 50% | 20% | 10% | 10% | 0% |
| 9 | TAA | F | 28 | 100% | 90% | 90% | 90% | 90% | 70% | 70% | 70% | 40% | 30% | 30% | 10% | 10% | 10% |
| | | | Total | 100% | 99% | 98% | 90% | 86% | 81% | 69% | 58% | 49% | 36% | 24% | 12% | 8% | 4% |
| 1 | ZAC | M | 15 | 100% | 100% | 100% | 100% | 80% | 80% | 60% | 60% | 60% | 40% | 30% | 30% | 10% | 0% |
| 2 | ZMP | M | 14 | 100% | 100% | 100% | 100% | 90% | 90% | 90% | 80% | 80% | 60% | 60% | 20% | 20% | 10% |
| 3 | MAP | M | 18 | 100% | 100% | 100% | 100% | 90% | 90% | 90% | 70% | 70% | 70% | 30% | 30% | 10% | 0% |
| 4 | CDC | M | 40 | 100% | 100% | 90% | 80% | 70% | 70% | 30% | 30% | 30% | 10% | 10% | 0% | 0% | 0% |
| 5 | CAC | M | 24 | 100% | 100% | 100% | 90% | 80% | 80% | 80% | 50% | 50% | 50% | 20% | 20% | 10% | 0% |
| 6 | RAA | M | 33 | 100% | 100% | 100% | 90% | 80% | 70% | 70% | 60% | 60% | 40% | 20% | 20% | 10% | 10% |
| | | | Total | 100% | 100% | 98% | 93% | 82% | 80% | 70% | 58% | 58% | 45% | 28% | 20% | 10% | 3% |
| | | | Totals | 100% | 99% | 98% | 91% | 84% | 81% | 69% | 58% | 53% | 39% | 26% | 15% | 9% | 4% |
| | | | | | | | Treatment Group | | | | | | | | | | |
| 1 | AAS | F | 34 | 100% | 30% | 20% | 10% | 0% | 0% | 0% | 0% | 0% | 0% | 0% | 0% | 0% | 0% |
| 2 | ACC | F | 36 | 100% | 20% | 0% | 0% | 0% | 0% | 0% | 0% | 0% | 0% | 0% | 0% | 0% | 0% |

TABLE I-continued

| # | Name | Gender | Age | Day 1 | Day 2 | Day 3 | Day 4 | Day 5 | Day 6 | Day 7 | Day 8 | Day 9 | Day 10 | Day 11 | Day 12 | Day 13 | Day 14 |
|---|------|--------|-----|-------|-------|-------|-------|-------|-------|-------|-------|-------|--------|--------|--------|--------|--------|
| 3 | AWC | F | 40 | 100% | 70% | 30% | 10% | 0% | 0% | 0% | 0% | 0% | 0% | 0% | 0% | 0% | 0% |
| 4 | BAB | F | 27 | 100% | 10% | 0% | 0% | 0% | 0% | 0% | 0% | 0% | 0% | 0% | 0% | 0% | 0% |
| 5 | CAB | F | 29 | 100% | 0% | 0% | 0% | 0% | 0% | 0% | 0% | 0% | 0% | 0% | 0% | 0% | 0% |
| 6 | CHH | F | 30 | 100% | 60% | 60% | 40% | 10% | 0% | 0% | 0% | 0% | 0% | 0% | 0% | 0% | 0% |
| 7 | DSF | F | 33 | 100% | 0% | 0% | 0% | 0% | 0% | 0% | 0% | 0% | 0% | 0% | 0% | 0% | 0% |
| 8 | GDL | F | 34 | 100% | 40% | 10% | 0% | 0% | 0% | 0% | 0% | 0% | 0% | 0% | 0% | 0% | 0% |
| 9 | HCD | F | 14 | 100% | 50% | 20% | 0% | 0% | 0% | 0% | 0% | 0% | 0% | 0% | 0% | 0% | 0% |
| 10 | HLL | F | 36 | 100% | 0% | 0% | 0% | 0% | 0% | 0% | 0% | 0% | 0% | 0% | 0% | 0% | 0% |
| 11 | JLP | F | 19 | 100% | 20% | 0% | 0% | 0% | 0% | 0% | 0% | 0% | 0% | 0% | 0% | 0% | 0% |
| 12 | JSH | F | 28 | 100% | 20% | 20% | 0% | 0% | 0% | 0% | 0% | 0% | 0% | 0% | 0% | 0% | 0% |
| 13 | JUL | F | 31 | 100% | 70% | 50% | 30% | 10% | 0% | 0% | 0% | 0% | 0% | 0% | 0% | 0% | 0% |
| 14 | KAC | F | 13 | 100% | 50% | 30% | 10% | 0% | 0% | 0% | 0% | 0% | 0% | 0% | 0% | 0% | 0% |
| 15 | KDJ | F | 20 | 100% | 20% | 0% | 0% | 0% | 0% | 0% | 0% | 0% | 0% | 0% | 0% | 0% | 0% |
| 16 | KEF | F | 26 | 100% | 10% | 0% | 0% | 0% | 0% | 0% | 0% | 0% | 0% | 0% | 0% | 0% | 0% |
| 17 | KFC | F | 17 | 100% | 0% | 0% | 0% | 0% | 0% | 0% | 0% | 0% | 0% | 0% | 0% | 0% | 0% |
| 18 | KST | F | 33 | 100% | 80% | 80% | 60% | 30% | 10% | 0% | 0% | 0% | 0% | 0% | 0% | 0% | 0% |
| 19 | LEF | F | 21 | 100% | 30% | 10% | 10% | 0% | 0% | 0% | 0% | 0% | 0% | 0% | 0% | 0% | 0% |
| 20 | LKD | F | 34 | 100% | 50% | 50% | 50% | 30% | 30% | 20% | 10% | 10% | 0% | 0% | 0% | 0% | 0% |
| 21 | LKJ | F | 15 | 100% | 70% | 40% | 20% | 10% | 0% | 0% | 0% | 0% | 0% | 0% | 0% | 0% | 0% |
| 22 | MDD | F | 35 | 100% | 20% | 0% | 0% | 0% | 0% | 0% | 0% | 0% | 0% | 0% | 0% | 0% | 0% |
| 23 | MDF | F | 19 | 100% | 50% | 10% | 0% | 0% | 0% | 0% | 0% | 0% | 0% | 0% | 0% | 0% | 0% |
| 24 | MEA | F | 38 | 100% | 70% | 30% | 20% | 20% | 10% | 0% | 0% | 0% | 0% | 0% | 0% | 0% | 0% |
| 25 | MLJ | F | 29 | 100% | 60% | 30% | 10% | 0% | 0% | 0% | 0% | 0% | 0% | 0% | 0% | 0% | 0% |
| 26 | NJM | F | 37 | 100% | 50% | 40% | 10% | 0% | 0% | 0% | 0% | 0% | 0% | 0% | 0% | 0% | 0% |
| 27 | RTY | F | 23 | 100% | 10% | 0% | 0% | 0% | 0% | 0% | 0% | 0% | 0% | 0% | 0% | 0% | 0% |
| 28 | SAH | F | 18 | 100% | 40% | 10% | 0% | 0% | 0% | 0% | 0% | 0% | 0% | 0% | 0% | 0% | 0% |
| 29 | SAL | F | 14 | 100% | 50% | 10% | 0% | 0% | 0% | 0% | 0% | 0% | 0% | 0% | 0% | 0% | 0% |
| 30 | SBH | F | 18 | 100% | 20% | 20% | 10% | 0% | 0% | 0% | 0% | 0% | 0% | 0% | 0% | 0% | 0% |
| 31 | SFH | F | 35 | 100% | 0% | 0% | 0% | 0% | 0% | 0% | 0% | 0% | 0% | 0% | 0% | 0% | 0% |
| 32 | SLB | F | 31 | 100% | 60% | 30% | 30% | 10% | 100% | 0% | 0% | 0% | 0% | 0% | 0% | 0% | 0% |
| 33 | TCA | F | 16 | 100% | 0% | 0% | 0% | 0% | 0% | 0% | 0% | 0% | 0% | 0% | 0% | 0% | 0% |
| 34 | TDB | F | 25 | 100% | 20% | 0% | 0% | 0% | 0% | 0% | 0% | 0% | 0% | 0% | 0% | 0% | 0% |
| 35 | TEM | F | 38 | 100% | 60% | 30% | 30% | 10% | 10% | 10% | 0% | 0% | 0% | 0% | 0% | 0% | 0% |
| 36 | TLS | F | 13 | 100% | 80% | 40% | 20% | 10% | 10% | 10% | 0% | 0% | 0% | 0% | 0% | 0% | 0% |
| 37 | TSJ | F | 36 | 100% | 50% | 30% | 10% | 10% | 0% | 0% | 0% | 0% | 0% | 0% | 0% | 0% | 0% |
| 38 | VYM | F | 21 | 100% | 80% | 80% | 80% | 50% | 30% | 10% | 10% | 10% | 0% | 0% | 0% | 0% | 0% |
| | Total | | | 100% | 37% | 21% | 12% | 5% | 5% | 1% | 1% | 1% | 0% | 0% | 0% | 0% | 0% |
| 1 | CAC | M | 40 | 100% | 20% | 10% | 0% | 0% | 0% | 0% | 0% | 0% | 0% | 0% | 0% | 0% | 0% |
| 2 | CDM | M | 39 | 100% | 60% | 40% | 10% | 10% | 0% | 0% | 0% | 0% | 0% | 0% | 0% | 0% | 0% |
| 3 | DAD | M | 16 | 100% | 20% | 10% | 0% | 0% | 0% | 0% | 0% | 0% | 0% | 0% | 0% | 0% | 0% |
| 4 | DDL | M | 21 | 100% | 0% | 0% | 0% | 0% | 0% | 0% | 0% | 0% | 0% | 0% | 0% | 0% | 0% |
| 5 | DFB | M | 35 | 100% | 80% | 80% | 40% | 20% | 10% | 10% | 10% | 10% | 0% | 0% | 0% | 0% | 0% |
| 6 | EHE | M | 14 | 100% | 20% | 0% | 0% | 0% | 0% | 0% | 0% | 0% | 0% | 0% | 0% | 0% | 0% |
| 7 | HAF | M | 33 | 100% | 60% | 60% | 20% | 20% | 10% | 10% | 0% | 0% | 0% | 0% | 0% | 0% | 0% |
| 8 | JEY | M | 15 | 100% | 20% | 20% | 10% | 0% | 0% | 0% | 0% | 0% | 0% | 0% | 0% | 0% | 0% |
| 9 | JKG | M | 18 | 100% | 40% | 10% | 10% | 0% | 0% | 0% | 0% | 0% | 0% | 0% | 0% | 0% | 0% |
| 10 | KEG | M | 36 | 100% | 0% | 0% | 0% | 0% | 0% | 0% | 0% | 0% | 0% | 0% | 0% | 0% | 0% |
| 11 | KSP | M | 31 | 100% | 30% | 30% | 10% | 10% | 0% | 0% | 0% | 0% | 0% | 0% | 0% | 0% | 0% |
| 12 | MJP | M | 34 | 100% | 20% | 20% | 10% | 0% | 0% | 0% | 0% | 0% | 0% | 0% | 0% | 0% | 0% |
| 13 | OAP | M | 20 | 100% | 90% | 40% | 20% | 10% | 0% | 0% | 0% | 0% | 0% | 0% | 0% | 0% | 0% |
| 14 | PLT | M | 38 | 100% | 70% | 50% | 30% | 10% | 10% | 0% | 0% | 0% | 0% | 0% | 0% | 0% | 0% |
| 15 | RAA | M | 21 | 100% | 20% | 20% | 0% | 0% | 0% | 0% | 0% | 0% | 0% | 0% | 0% | 0% | 0% |
| 16 | RDC | M | 30 | 100% | 30% | 10% | 10% | 0% | 0% | 0% | 0% | 0% | 0% | 0% | 0% | 0% | 0% |
| 17 | RCJ | M | 25 | 100% | 60% | 20% | 20% | 20% | 10% | 0% | 0% | 0% | 0% | 0% | 0% | 0% | 0% |
| 18 | TFL | M | 16 | 100% | 0% | 0% | 0% | 0% | 0% | 0% | 0% | 0% | 0% | 0% | 0% | 0% | 0% |
| 19 | SHT | M | 28 | 100% | 20% | 10% | 0% | 0% | 0% | 0% | 0% | 0% | 0% | 0% | 0% | 0% | 0% |
| 20 | DKP | M | 36 | 100% | 50% | 10% | 10% | 0% | 0% | 0% | 0% | 0% | 0% | 0% | 0% | 0% | 0% |
| 21 | WRT | M | 28 | 100% | 30% | 10% | 0% | 0% | 0% | 0% | 0% | 0% | 0% | 0% | 0% | 0% | 0% |
| 22 | WJK | M | 32 | 100% | 80% | 80% | 60% | 40% | 40% | 20% | 20% | 10% | 10% | 0% | 0% | 0% | 0% |
| 23 | PLL | M | 24 | 100% | 20% | 0% | 0% | 0% | 0% | 0% | 0% | 0% | 0% | 0% | 0% | 0% | 0% |
| 24 | MWT | M | 31 | 100% | 0% | 0% | 0% | 0% | 0% | 0% | 0% | 0% | 0% | 0% | 0% | 0% | 0% |
| 25 | TIM | M | 26 | 100% | 10% | 10% | 0% | 0% | 0% | 0% | 0% | 0% | 0% | 0% | 0% | 0% | 0% |
| 26 | BTL | M | 37 | 100% | 60% | 30% | 10% | 10% | 0% | 0% | 0% | 0% | 0% | 0% | 0% | 0% | 0% |
| 27 | DWD | M | 22 | 100% | 70% | 20% | 20% | 10% | 0% | 0% | 0% | 0% | 0% | 0% | 0% | 0% | 0% |
| | Total | | | 100% | 36% | 22% | 11% | 6% | 3% | 1% | 1% | 1% | 0% | 0% | 0% | 0% | 0% |
| | Totals | | | 100% | 37% | 21% | 11% | 6% | 4% | 1% | 1% | 1% | 0% | 0% | 0% | 0% | 0% |

EXAMPLE 3

The inventors have tested the device on multiple oral herpes lesions of human volunteers, and the results have shown a complete termination of the herpetic lesion after two applications of the device at 2½ minutes per treatment, 12 hours apart, as described in Example 2. The volunteers reported a marked decrease in healing time after treatment versus the usual healing cycle for lesions of this type.

All of the compositions and methods disclosed and claimed herein can be made and executed without undue experimentation in light of the present disclosure. While the compositions and methods of this invention have been described in terms of preferred embodiments, it will be apparent to those of skill in the art that variations can be applied to the devices or methods and in the steps or in the sequence of steps of the methods described herein without departing from the concept, spirit and scope of the invention. More specifically, it will be apparent that certain mechanical elements related to those described above can be substituted for the mechanical elements described herein to achieve the same or similar results. All such similar substitutes and modifications apparent to those skilled in the art are deemed to be within the spirit, scope and concept of the invention as defined by the appended claims.

What is claimed is:

1. A method of treating a skin lesion, comprising:
   (a) applying thermal energy to the lesion with a device, wherein the thermal energy is provided by a heating element in thermal contact with an interface contacting the skin of a subject having the lesion; and
   (b) delivering an effective therapeutic amount of thermal energy to the lesion during a treatment that is sufficient to reduce the size of the lesion by about 100% on or before the 9$^{th}$ day post treatment.

2. The method of claim 1 wherein the effective therapeutic amount of thermal energy delivered to the lesion is sufficient to reduce the size of the lesion by about 100% on or before the 8$^{th}$ day post treatment.

3. The method of claim 1 wherein the effective therapeutic amount of thermal energy delivered to the lesion is sufficient to reduce the size of the lesion by about 100% on or before the 7$^{th}$ day post treatment.

4. The method of claim 1 wherein the effective therapeutic amount of thermal energy delivered to the lesion is sufficient to reduce the size of the lesion by about 100% on or before the 6$^{th}$ day post treatment.

5. The method of claim 1 wherein the skin lesion is a viral infection.

6. The method of claim 5 wherein the viral infection is a cold sore.

7. The method of claim 1 wherein the skin lesion is a fungal infection.

8. The method of claim 1 wherein the skin lesion is caused by an irritant.

9. The method of claim 8 wherein the irritant is introduced thought the bite of an insect.

10. The method of claim 1 wherein the skin lesion is a bacterial infection.

11. The method of claim 1, wherein the skin lesion is acne.

12. A method for treating skin lesions comprising:
    providing an interface for contacting the skin of a subject, wherein the interface is interchangeable or disposable;
    providing a heating element in thermal contact with the interface, such that the interface can be heated to a temperature from a range of about 48° C. to about 53° C.;
    providing a heater control system capable of maintaining the interface at a temperature between about 48° C. to about 53° C. for at least 20 seconds; and
    providing an input/output system allowing a user to select a pre-programmed setting from a plurality of preprogrammed parameters and to variably adjust a pre-programmed parameter of the setting within a predetermined safe range, wherein each pre-programmed setting provides a treatment optimized for a particular type of skin lesion.

13. A method for treating skin lesions comprising:
    providing an interface for contacting the skin of a subject, wherein the interface has a surface area of less than about 0.5 cm$^2$;
    providing a heating element in thermal contact with the interface, such that the interface can be heated to a temperature from a range of about 48° C. to about 53° C.;
    providing a heater control system capable of maintaining the interface at a temperature between about 48° C. to about 53° C. for at least 20 seconds; and
    providing an input/output system allowing a user to select a pre-programmed setting from a plurality of preprogrammed parameters and to variably adjust a pre-programmed parameter of the setting within a predetermined safe range, wherein each pre-programmed setting provides a treatment optimized for a particular type of skin lesion.

14. The method of claim 13 wherein the interface is interchangeable or disposable.

15. A method for treating skin lesions comprising:
    providing an interface for contacting the skin of a subject, wherein the heater control system is capable of maintaining the interface at a temperature between about 48° C. to about 53° C. for at least 150 seconds;
    providing a heating element in thermal contact with the interface, such that the interface can be heated to a temperature from a range of about 48° C. to about 53° C.;
    providing a heater control system capable of maintaining the interface at a temperature between about 48° C. to about 53° C. for at least 20 seconds; and
    providing an input/output system allowing a user to select a pre-programmed setting from a plurality of preprogrammed parameters and to variably adjust a pre-programmed parameter of the setting within a predetermined safe range, wherein each pre-programmed setting provides a treatment optimized for a particular type of skin lesion.

16. The method of claim 12 wherein the heater control system uses a feedback control mechanism involving the use of PID control algorithms.

* * * * *